(12) United States Patent
Hembre et al.

(10) Patent No.: US 9,340,482 B2
(45) Date of Patent: *May 17, 2016

(54) PROCESSES FOR MAKING CYCLOHEXANE COMPOUNDS

(71) Applicant: Eastman Chemical Company, Kingsport, TN (US)

(72) Inventors: Robert Thomas Hembre, Johnson City, TN (US); Venkata Bharat Ram Boppana, Johnson City, TN (US); Scott Donald Barnicki, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 320 days.

This patent is subject to a terminal disclaimer.

(21) Appl. No.: 14/143,936

(22) Filed: Dec. 30, 2013

(65) Prior Publication Data

US 2015/0183706 A1 Jul. 2, 2015

(51) Int. Cl.
*C07C 51/36* (2006.01)

(52) U.S. Cl.
CPC ............. *C07C 51/36* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 2,109,844 A | 3/1938 | Lazier | |
| 2,139,369 A | 12/1938 | Kyrides | |
| 2,221,882 A | 11/1940 | Rosenberg | |
| 2,446,430 A | 8/1948 | Norton | |
| 2,675,390 A | 4/1954 | Rosenblatt | |
| 2,687,430 A | 8/1954 | Snow et al. | |
| 2,789,509 A | 4/1957 | Reynolds et al. | |
| 2,814,649 A | 11/1957 | Pritchard | |
| 2,828,335 A | 3/1958 | Ferstandig et al. | |
| 2,877,190 A | 3/1959 | Canterino | |
| 2,888,484 A | 5/1959 | Dehm et al. | |
| 2,939,886 A | 6/1960 | Pritchard et al. | |
| 3,162,679 A | 12/1964 | Rylander et al. | |
| 3,267,157 A | 8/1966 | Miya | |
| 3,326,972 A | 6/1967 | Schenk et al. | |
| 3,334,149 A | 8/1967 | Akin et al. | |
| 3,444,237 A | 5/1969 | Jaffe | |
| 3,520,921 A | 7/1970 | Appell | |
| 3,557,222 A | 1/1971 | Withers, Jr. e al. | |
| 3,560,429 A | 2/1971 | Bilow et al. | |
| 3,607,917 A | 9/1971 | Buls | |
| 3,993,699 A | 11/1976 | Maeda et al. | |
| 4,053,510 A | 10/1977 | Zengel et al. | |
| 4,149,021 A | 4/1979 | Wall | |
| 4,239,703 A | 12/1980 | Bernhardt et al. | |
| 4,283,565 A | 8/1981 | Bernhardt et al. | |
| 4,301,088 A | 11/1981 | Bernhardt | |
| 4,431,798 A | 2/1984 | Paschke et al. | |
| 4,611,085 A | 9/1986 | Kitson | |
| 4,754,064 A | 6/1988 | Lillwitz | |
| 4,804,791 A | 2/1989 | Kitson et al. | |
| 4,837,367 A | 6/1989 | Gustafson et al. | |
| 4,837,368 A | 6/1989 | Gustafson et al. | |
| 4,929,777 A | 5/1990 | Irick, Jr. et al. | |
| 4,973,717 A | 11/1990 | Williams | |
| 5,118,841 A | 6/1992 | Cook et al. | |
| 5,202,475 A | 4/1993 | Cook et al. | |
| 5,278,339 A | 1/1994 | Cook | |
| 5,286,898 A | 2/1994 | Gustafson et al. | |
| 5,334,779 A | 8/1994 | Kuo | |
| 5,387,752 A | 2/1995 | Scarlett et al. | |
| 5,430,184 A | 7/1995 | Tateno et al. | |
| 5,763,353 A | 6/1998 | Kadono et al. | |
| 5,929,274 A | 7/1999 | Lamshing et al. | |
| 6,113,866 A | 9/2000 | Lee et al. | |
| 6,187,968 B1 | 2/2001 | Itoh et al. | |
| 6,284,932 B1 | 9/2001 | Fischer et al. | |
| 6,291,706 B1 | 9/2001 | Sumner, Jr. et al. | |
| 6,294,703 B1 | 9/2001 | Hara et al. | |
| 6,495,730 B1 | 12/2002 | Konishi et al. | |
| 6,600,080 B1 | 7/2003 | Nagamura et al. | |
| 6,797,844 B2 | 9/2004 | Nakai | |
| 6,919,489 B1 | 7/2005 | McCusker-Orth | |
| 7,615,671 B2 | 11/2009 | Puckette et al. | |
| 2005/0234269 A1 | 10/2005 | Kilner et al. | |
| 2010/0286287 A1 | 11/2010 | Walden | |
| 2012/0296111 A1 | 11/2012 | Königsmann et al. | |

(Continued)

FOREIGN PATENT DOCUMENTS

| | | |
|---|---|---|
| CN | 1911885 A | 2/2007 |
| CN | 101812170 A | 8/2010 |
| EP | 0 225 802 A2 | 6/1987 |

(Continued)

OTHER PUBLICATIONS

Brindell, Gordon D. et al.; "Polymer Applications of Some Terephthalaldehyde Derivatives": Ind. Eng. Chem., Prod. Res. Dev., vol. 15, No. 1; 1976; pp. 83-88.

(Continued)

*Primary Examiner* — Sudhakar Katakam
*Assistant Examiner* — Jennifer C Sawyer
(74) *Attorney, Agent, or Firm* — James Arnold, Jr.

(57) ABSTRACT

This invention relates to hydrogenation processes for making cyclohexane compounds. More specifically, this invention relates to hydrogenation processes in the presence of tertiary amide solvent compounds, as well as compositions that can result from such processes. The invention thus provides processes for making cyclohexanecarboxylic acid compounds and processes for making hydroxymethylcyclohexane compounds.

33 Claims, 1 Drawing Sheet

(56) References Cited

U.S. PATENT DOCUMENTS

| | | |
|---|---|---|
| 2013/0029831 A1 | 1/2013 | Kilner et al. |
| 2013/0030222 A1 | 1/2013 | Barton et al. |

FOREIGN PATENT DOCUMENTS

| | | |
|---|---|---|
| EP | 0 523 818 B2 | 8/2000 |
| GB | 1 254 927 | 11/1971 |
| JP | 2001-181223 A | 7/2001 |
| JP | 2002-60356 A | 2/2002 |
| JP | 2002-69016 A | 3/2002 |
| JP | 2004-300130 A | 10/2004 |

OTHER PUBLICATIONS

Harper, Jon Jay and Janik, Paul; "Terephthalic Acid Solubility"; Journal of Chemical and Engineering Data, vol. 15, No. 3; 1970; pp. 439-440.

Kibler, Charles J. et al.; "Polyesters of 1,4-Cyclohexanedimethanol"; Journal of Polymer Science: Part A, vol. 2; 1964; pp. 2115-2125.

Li, Dian-Qing et al.; "Solubilities of Terephthalaldehydic, p-Toluic, Benzoic, Terephthalic, and Isophthalic Acids in N-Methyl-2-pyrrolidone from 295.65 K to 371.35K"; Journal of Chemical Engineering Data, vol. 46; 2001; pp. 172-173.

Pinkus, A. G. and Hariharan, Rajan; Poly-3- and 4-hydroxymethlybenzoates: Future Engineering/Fiber "Plastics"?; Journ. Macro. Sci.—Rev. Macromol. Chem. Phys., C33(3); 1993; pp. 259-289.

Prasad, Ram and Singh, Pratichi; "Applications and Preparation Methods of Copper Chromite Catalysts: A Review"; Bulletin of Chemical Reaction Engineering & Catalysis, vol. 6, No. 2; 2011; pp. 63-113.

Satchell, D. P. N. and Satchell, R. S.; "Quantitative Aspects of the Lewis Acidity of Covalent Metal Halides and Their Organo Derivatives"; Chemical Reviews, vol. 69, No. 3; Jun. 1969; pp. 251-278.

Turner, S. Richard; "Development of Amorphous Copolyesters Based on 1,4-Cyclohexanedimethanol"; Journal of Polymer Science: Part A: Polymer Chemistry, vol. 42; 2004; pp. 5847-5852.

Twigg, Martyn V. and Spencer, Michael S.; "Deactivation of supported copper metal catalysts for hydrogenation reactions"; Applied Catalysis A: General, vol. 212; 2001; pp. 161-174.

Properties & Uses for Terephthalic Acid, Sevas Educational Society retrieved from http://www.sbioinformatics.com/design_thesis/Terephthalic_acid/Terephthalic-2520acid_Properties&uses.pdf, Accessed Dec. 7, 2012.

Notification of Transmittal of the International Search Report and the Written Opinion of the International Searching Authority, or the Declaration date of mailing Mar. 23, 2015 received in corresponding International Patent Application No. PCT/US2014/070731.

Notification of Transmittal of the International Search Report and the Written Opinion of the International Searching Authority, or the Declaration date of mailing Mar. 30, 2015 received in corresponding International Patent Application No. PCT/US2014/070733.

Co-pending U.S. Appl. No. 14/143,914, filed Dec. 30, 2013; Robert Thomas Hembre, et al.; now U. S. Patent Publication No. 2015-0183699.

Co-pending U.S. Appl. No. 14/581,369, filed Dec. 23, 2014; Robert Thomas Hembre et al.

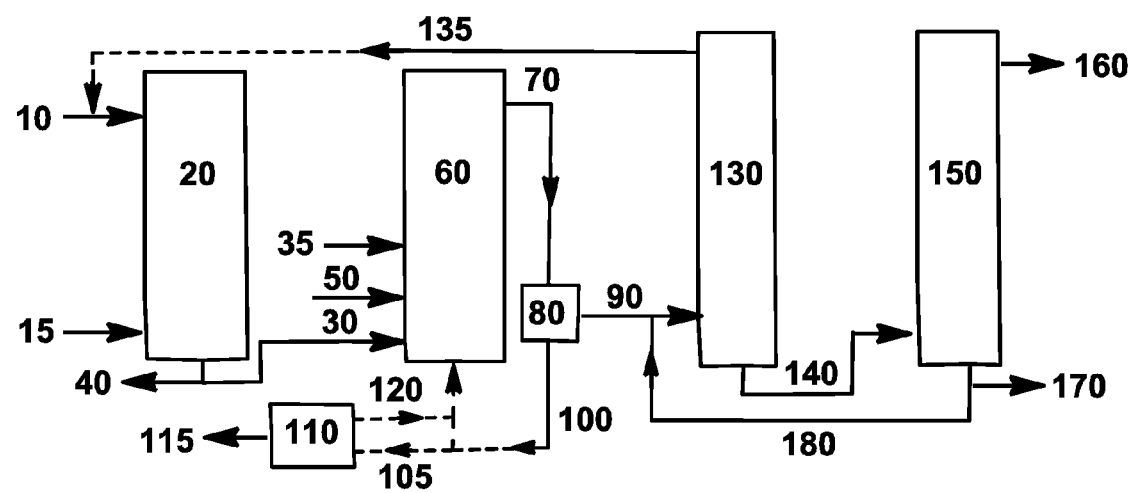

PROCESSES FOR MAKING CYCLOHEXANE COMPOUNDS

FIELD OF THE INVENTION

This invention relates to hydrogenation processes for making cyclohexane compounds. More specifically, this invention relates to hydrogenation processes in the presence of tertiary amide solvent compounds, as well as compositions that can result from such processes.

BACKGROUND OF THE INVENTION

Cyclohexanecarboxylic acid compounds and hydroxymethylcyclohexane compounds are important commercial chemicals. For example, diacids such as 1,4-cyclohexanedicarboxylic acid (CHDA) and 1,3-cyclohexanedicarboxylic acid and diols such as 1,4-cyclohexanedimethanol (CHDM) are useful monomers in formation of a wide variety of polymers and intermediates in a variety of additional reactions. 1,4-CHDA production can act as an intermediate for the synthesis of 1,4-cyclohexanedimethanol (CHDM). The monoacid cyclohexanecarboxylic acid is used as a raw material in synthesis of other compounds, and cyclohexanecarboxylic acid and several of its derivatives are useful as flavor and fragrance agents. Many cyclohexanecarboxylic acid compounds are prepared by hydrogenation of benzenecarboxylic acids. For example, there exists processes for synthesis of 1,4-CHDA from terephthalic acid (TPA). Many such processes suffer the drawback that they use compounds that are poor solvents for TPA. Processes also exist that include the conversion of TPA to its alkaline metal salts, and subsequent hydrogenation of such salts. Such processes, however, involve an additional process step as well as issues associated with conversion back to acids and removal and management of inorganic salts and acids in the process. Thus, there is a continuing need for improvement of processes for making cyclohexanecarboxylic acid and hydroxymethylcyclohexane compounds.

BRIEF SUMMARY OF THE INVENTION

Processes are provided involving use of tertiary cyclic amide solvent compounds as solvents in hydrogenation reactions. Such reactions demonstrate significantly more favorable results than other compounds having solubility characteristics similar to that of tertiary cyclic amide solvent compounds.

The invention thus provides processes for making at least one cyclohexanecarboxylic acid compound that include combining at least one benzenecarboxylic acid compound, at least one solvent and hydrogen in the presence of at least one aryl hydrogenation catalyst under conditions effective to hydrogenate the benzene ring on at least some of the at least one benzenecarboxylic acid compound, wherein the at least one aryl hydrogenation catalyst includes at least one rhodium or ruthenium compound on a solid support and the at least one solvent includes at least one tertiary cyclic amide solvent compound.

The invention further provides processes for making at least one hydroxymethylcyclohexane compound includes combining hydrogen with:
a. at least one cyclohexanecarboxylic acid compounds and
b. at least one solvent that includes at least one tertiary cyclic amide solvent compound, in the presence of at least one acid hydrogenation catalyst under conditions effective to hydrogenate carboxylic acid groups on at least some of the at least one cyclohexanecarboxylic acid compounds.

The invention further provides processes for making at least one hydroxymethylcyclohexane compound, the process including:

a. combining hydrogen, at least one benzenecarboxylic acid compound and at least one solvent in the presence of at least one aryl hydrogenation catalyst containing at least one rhodium or ruthenium compound on a solid support in a first reaction zone under first reaction conditions effective to hydrogenate the benzene ring on at least some of the at least one benzenecarboxylic acid compound to produce a first composition containing at least one cyclohexanecarboxylic acid and the at least one solvent;

b. combining at least some of the first composition with hydrogen and an acid hydrogenation catalyst in a second reaction zone under second reaction conditions effective to hydrogenate the acid groups on at least some of the at least one cyclohexanecarboxylic acid to produce a second composition containing at least one hydroxymethylcyclohexane compound and the at least one solvent, wherein the solvent contains at least one tertiary cyclic amide solvent compound. In some embodiments of the type described by this paragraph, at least about 50% of the at least one solvent fed to first reaction zone is fed to the second reaction zone, and in some embodiments, at least about 80% of the at least one solvent fed to first reaction zone is fed to the second reaction zone. In some embodiments of the type described by this paragraph, the process further includes processing the second composition in at least one first separation zone to remove at least some of the catalyst from the second composition. In some embodiments of the type described by this paragraph, the process further includes processing at least some of the second composition in at least one second separation zone to concentrate the hydroxymethylcyclohexane compound in a crude product stream and to concentrate the at least one solvent compound in a recovered solvent stream. In some embodiments of the type described in the previous sentence, the process further includes recycling at least some of the recovered solvent stream to the first hydrogenation zone.

In some embodiments of the methods, at least one tertiary cyclic amide solvent compound has the structure depicted in formula I or II:

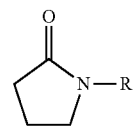

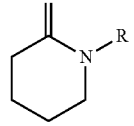

wherein R is selected from alkyl, cycloalkyl, aryl, aryl-substituted alkyl, cycloalkyl-substituted alkyl, alkyl-substituted aryl, and alkyl-substituted cycloalkyl, and wherein R has from 1 to 10 carbon atoms and optionally possesses one hydroxyl group. In some embodiments, R has one or two carbon atoms. In some embodiments, R is an unsubstituted alkyl group. In some embodiments, R is methyl or ethyl. In some embodiments, R is 2-hydroxyethyl. In some embodiments, the at least one tertiary amide solvent compound has the structure depicted in formula I.

In some embodiments of the above processes at least about 50% by weight of the solvent is at least one tertiary cyclic amide solvent compound. In some embodiments, at least about 80% by weight of the solvent is at least one tertiary cyclic amide solvent compound. In some embodiments, the solvent further includes isopropyl alcohol.

In some embodiments of the processes that involve at least one benzenecarboxylic acid compound, the at least one benzenecarboxylic acid compound includes at least one monoacid. In some embodiments, the at least one benzenecarboxylic acid compound includes at least one diacid. In some embodiments, the at least one diacid is selected from terephthalic acid, isophthalic acid, or combinations thereof. In some embodiments, the at least one diacid is isophthalic acid. In some embodiments, the at least one diacid is terephthalic acid.

In some embodiments, the at least one cyclohexanecarboxylic acid compound includes 1,4 cyclohexanedicarboxylic acid. In some embodiments, the at least one cyclohexanecarboxylic acid compound includes 1,3 cyclohexanedicarboxylic acid. In some embodiments, the at least one cyclohexanecarboxylic acid compound includes a blend of 1,3 cyclohexanedicarboxylic acid and 1,4 cyclohexanedicarboxylic acid.

In some embodiments of processes that include at least one aryl hydrogenation catalyst, the at least one aryl hydrogenation catalyst includes at least one ruthenium compound on a solid support. In some embodiments, the solid support is carbon. In some embodiments of the type described in this paragraph, conditions effective to hydrogenate the benzene ring on at least some of the at least one benzenecarboxylic acid compound include pressure of from about 1,000 to about 1,500 psig and temperature of from about 80 to about 190° C.

In some embodiments of processes that include at least one aryl hydrogenation catalyst, the at least one aryl hydrogenation catalyst includes at least one aryl hydrogenation catalyst includes at least one rhodium compound on a solid support. In some embodiments, the solid support is carbon. In some embodiments of the type described in this paragraph, conditions effective to hydrogenate the benzene ring on at least some of the at least one benzenecarboxylic acid compound include pressure of from about 400 to about 600 psig and temperature of from about 80 to about 120° C. In some embodiments of the type described in the first sentence of this paragraph, the solvent further includes isopropyl alcohol and conditions effective to hydrogenate the benzene ring on at least some of the at least one benzenecarboxylic acid compound include pressure of from about 150 to about 400 psig and temperature of from about 80 to about 120° C.

In some embodiments that involve an acid hydrogenation catalyst, the acid hydrogenation catalyst includes (a) a ruthenium compound; and (b) a tridentate triphosphine compound selected from 1,1,1-tris(diarylphosphinomethyl)alkyl in which the alkyl is substituted or unsubstituted. In some embodiments, the ruthenium compound and the tridentate triphosphine compound are the same compound. In some embodiments, wherein the ruthenium compound is selected from ruthenium carboxylates, ruthenium acetylacetones, ruthenium hydride complexes, ruthenium carbonyl compounds, ruthenium halides, ruthenium oxides, ruthenium phosphine complexes, and compositions of two or more of the foregoing; and the tridentate triphosphine compound is selected from tris(diphenylphosphinomethyl)alkyl or substituted alkyl. In some embodiments, ruthenium compound includes ruthenium(III)acetylacetonate. In some embodiments, the tridentate triphosphine compound includes 1,1,1-tris(diphenylphosphinomethyl)ethane. In some embodiments, the ruthenium compound is selected from ruthenium carboxylates, ruthenium acetylacetones, ruthenium hydride complexes, ruthenium carbonyl compounds, ruthenium halides, ruthenium oxides, ruthenium phosphine complexes, and compositions of two or more of the foregoing; and the tridentate triphosphine compound is selected from tris(diphenylphosphinomethyl)alkyl or substituted alkyl. In some embodiments, the ruthenium compound includes ruthenium(III)acetylacetonate. In some embodiments, the tridentate triphosphine compound includes 1,1,1-tris(diphenylphosphinomethyl)ethane.

In some embodiments that involve an acid hydrogenation catalyst the process further includes combining the acid hydrogenation catalyst with a promoter selected from Lewis acids, protic acids having an ionization constant ($K_i$) of $5 \times 10^{-3}$ or greater, onium salts, and compositions of two or more of the foregoing. In some embodiments, the promoter is selected from ammonium hexafluorophosphate, tetrabutylammonium hexafluorophosphate, tetraphenylphosphonium bromide, sodium tetraphenyl borate, ammonium tetrafluoroborate, tetramethyl ammonium tetrafluoroborate, toluenesulfonic acid, phosphoric acid, triflic acid, sulfuric acid, methanesulfonic acid, trifluoroacetic acid, dodecylbenzenesulfonic acid, dinonylnaphthalenesulfonic acid, and compositions of two or more of the foregoing. In some embodiments, wherein the promoter is selected from tetrabutylammonium hexafluorophosphate, triflic acid, toluenesulfonic acid, dodecylbenzenesulfonic acid, dinonylnaphthalenesulfonic acid, and compositions of two or more of the foregoing.

In some embodiments that involve an acid hydrogenation catalyst, the acid hydrogenation is performed under reaction conditions that include a pressure of from about 500 to about 3,000 psig and a temperature of from about 100 to about 240° C.

The invention further provides compositions that include at least one cyclohexanecarboxylic acid and a solvent of any of the types described above. The invention further provides compositions that include at least one hydoxymethylcyclohexane compound and a solvent of any of the types described above.

BRIEF DESCRIPTION OF THE DRAWING

FIG. 1 is a depiction of one embodiment of the invention in which a benzenecarboxylic acid is hydrogenated to result in a cyclohexanedicarboxylic acid compound which is, in turn, hydrogenated to result in a hydroxymethylcyclohexane compound.

DETAILED DESCRIPTION

The invention provides processes that include hydrogenation reactions in the presence of at least one tertiary cyclic amide solvent compound. In some embodiments, the process includes hydrogenation of the unsaturated carbons on the benzene ring of at least one benzenecarboxylic acid in the presence of the tertiary cyclic amide solvent compound to form a cyclohexanecarboxylic acid compound. In some embodiments, the process includes hydrogenation of at least one carboxylic acid group on at least one cyclohexanecarboxylic acid compound in the presence of the tertiary cyclic amide solvent compound to form a hydroxymethylcyclohexane compound. The invention further provides two-step processes in which the benzene ring of at least one benzenecarboxylic acid compound is hydrogenated to form at least one cyclohexanecarboxylic acid compound, and one or more acid group on the at least one cyclohexanecarboxylic acid compound is then further hydrogenated in a second step to form at least one hydroxymethylcyclohexane compound from the first step, and both steps are performed in the presence of a tertiary cyclic amide solvent compound. Because the solvents can be the same in both steps, the invention further provides embodiments in which the second step is performed in the presence of some, most or substantially all of the solvent that was present in the first step. The invention thus may afford the opportunity in some embodiments to reduce or to eliminate separation of the cyclohexanecarboxylic acid compounds from the solvent used in the first step.

Solvents and Tertiary Cyclic Amide Solvent Compounds

The solvent in the hydrogenation process includes a tertiary cyclic amide solvent compound. As used throughout this application, "cyclic amide solvent compounds" or "cyclic amide compounds" refers to cyclic compounds (commonly referred to as lactam compounds) containing an amide group in which both the nitrogen of the amide group and the carbon of the carbonyl moiety of the amide group are members of the cyclic rings. Some examples include four membered rings based on β-lactam (2-azetidinone), five membered rings based on γ-lactam (2-pyrrolidone), six membered rings based on δ-lactam (2-piperidone) and seven membered rings based on ε-lactam (azepan-2-one or caprolactam) compounds. The cyclic amide solvent compounds of the present invention are tertiary cyclic amides, meaning that the nitrogen atom in the amide is bonded to three carbon atoms. Two of the carbon atoms are members of the ring, and the third carbon is part of a group referred to as "R," herein. For example, tertiary amides based on 2-pyrrolidone and 2-piperidone have the structure shown in formula I and II:

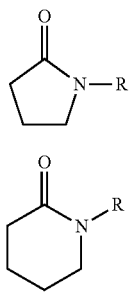

Although 2-pyrrolidone and 2-piperidone are used as illustrations above, embodiments exist in which other tertiary cyclic amide solvent compounds are used, and the descriptions of the R group herein can apply to the corresponding group on any tertiary cyclic amide. As used throughout this application, "tertiary cyclic amide solvent compounds" refers to all such compounds. In some embodiments, the tertiary cyclic amide solvent compound is selected from compounds having the structure shown in formula I or II or combinations of two or more thereof. In some embodiments, the tertiary cyclic amide solvent compound is selected from compounds having the structure shown in formula I or combinations of two or more thereof. In some embodiments, the tertiary cyclic amide solvent compound is selected from compounds having the structure shown in formula II or combinations of two or more thereof.

The R group in the tertiary cyclic amide solvent compound is selected from substituted or unsubstituted alkyl, cycloalkyl, aryl, aryl-substituted alkyl, cycloalkyl-substituted alkyl, alkyl-substituted aryl, and alkyl-substituted cycloalkyl, and wherein R has 1 to 10 carbon atoms and optionally possesses one or more hydroxyl (—OH) groups. In some embodiments, the R group possesses a single terminal hydroxyl group (i.e. a hydroxyl group bonded to a carbon that is furthest from the nitrogen). Embodiments exist in which R is an alkyl having 1 to 10 carbon atoms, 1 to 6 carbon atoms, 1 to 4 carbon atoms, 1 to 3 carbon atoms or 1 to 2 carbon atoms, each of the foregoing having embodiments that possess a terminal hydroxyl groups and embodiments that do not. Embodiments of each of these exist in which the alkyl group includes a hydroxyl group or where it does not. Some examples of alkyl groups suitable for R include methyl, ethyl, n-propyl, isopropyl, n-butyl, isobutyl, tert-butyl, n-pentyl, n-hexyl, n-heptyl, n-octyl, and 2-hydroxyethyl. In some embodiments, R is selected from methyl and ethyl. In some embodiments, R is selected from methyl, ethyl, and 2-hydroxyethyl. In some embodiments, R is methyl (e.g. n-methyl-2-pyrrolidone or n-methyl-2-piperidone). In some embodiments, R is ethyl (e.g. n-ethyl-2-pyrrolidone or n-ethyl-2-piperidone). In some embodiments, R is 2-hydroxyethyl (e.g. n-2-hydroxyethyl-2-pyrrolidone or n-2-hydroxyethyl-2-piperidone). Combinations of two or more compounds of the foregoing description may also be used, including combinations of compounds having differing R groups.

In some embodiments, the at least one tertiary cyclic amide solvent compound constitute(s) at least about 50% of the solvent. In some embodiments, the at least one tertiary cyclic amide solvent compound constitute(s) at least about 75% of the solvent. In some embodiments, the at least one tertiary cyclic amide solvent compound constitute(s) at least about 85% of the solvent. In some embodiments, the at least one tertiary cyclic amide solvent compound constitute(s) at least about 90% of the solvent. In some embodiments, the at least one tertiary cyclic amide solvent compound constitute(s) at least about 95% of the solvent. A tertiary cyclic amide solvent compound may be used alone, in blends of two or more tertiary cyclic amide solvent compounds, in blends with any other types of solvent compounds, or both. Where other compounds are used in the solvent, the identity is not critical and any compound that does not unacceptably interfere with the hydrogenation reaction. Some examples include water, methanol, ethanol, n-propanol, isopropyl alcohol, and n-butanol. In some embodiments, the at least one additional solvent compound includes at least one secondary alcohol. In some embodiments, the secondary alcohol has from 1 to 8 carbon atoms. Embodiments exist in which the secondary alcohol is isopropyl alcohol, 2-butanol, 3-pentanol, 2-pentanol, 3-hexanol, 2-hexanol or skeletal isomers thereof or a cyclopentanol, or a cyclohexanol thereof or combinations of two or more of the foregoing. In some embodiments, the amount of solvent includes from about 1.0 to about 40 weight percent of at least one secondary alcohol. Embodiments exist in which the amount of at least one secondary alcohol is from about 1.0 to about 30, from about 1.0 to about 20, from about 1.0 to about 15 weight percent, from about 1.0 to about 10 weight percent, from about 10 to about 40 weight percent, from about 10 to about 30 weight or from about 5.0 to about 20 weight percent based on the total weight of the solvent.

The solvent compounds are part of the feed to a hydrogenation process and are present in an amount effective to provide adequate dissolution or suspension of the feed materials. In some embodiments, the solvent compounds together (i.e. the one or more tertiary cyclic amide solvent compounds and any other solvent compounds) is at least about 50 wt. % of the feed to the hydrogenation process. Embodiments also exist in which the solvent compounds are at least about 75 wt. %, at least about 80 wt. % or at least about 90 wt. % of the feed to the hydrogenation process.

Hydrogenation of Benzenecarboxylic Acids

In some embodiments, the process includes hydrogenation of the benzene ring carbons of at least one benzenecarboxylic acid. In such embodiments, the process includes combining at least one benzenecarboxylic acid compound, at least one solvent and hydrogen in the presence of an aryl hydrogenation catalyst wherein the solvent has the characteristics described above. As used throughout this application, "benzenecarboxylic acid" means a compound containing a six carbon aromatic ring or "benzene ring" in which at least one of the carbons in the ring is covalently bonded to the carbon of a carboxylic acid group. In some embodiments, the compound has a single carboxylic acid group bonded thereto. In some embodiments, the compound has two carboxylic acid groups bonded thereto. In some embodiments, the compound has 3 carboxylic acid groups bonded thereto. Embodiments also exist in which the number of carboxylic acid groups may be described as a range, such as 1 to 3, 1 to 6 or 1 to 2. Some examples of benzenecarboxylic acids include: the monoacids benzoic acid, 2-methylbenzoic acid, 3-methylbenzoic acid, 4-methylbenzoic acid, ethyl benzoic acid, 4-carboxybenzaldehyde, p-hydroxymethylbenzoic acid and 2-methyl terephthalic acid; the diacids benzene-1,4-dicarboxylic acid (terephthalic acid), benzene-1,3-dicarboxylic acid (isophthalic acid) and benzene-1,2-dicarboxylic acid (phthalic acid); the triacids trimellitic acid and hemimellitic; and other poly acids such as trimesic acid, as well as any combination of any two or more of the foregoing. In some embodiments, the at least one benzenecarboxylic acid includes one or more diacids. In some embodiments, the benzenecarboxylic acid is selected from terephthalic acid, isophthalic acid or combinations thereof. In some embodiments, the benzenecarboxylic acid is terephthalic acid. In some embodiments, the benzenecarboxylic acid is isophthalic acid. In some embodiments, the benzenecarboxylic acid is a blend of terephthalic acid and isophthalic acid. In some embodiments, the benzenecarboxylic acid is benzoic acid. Specific embodiments of the process exist for each of the foregoing, and embodiments exist for blends of any two or more of the foregoing.

The hydrogenation of the benzenecarboxylic acid occurs in the presence of an aryl hydrogenation catalyst. The aryl hydrogenation catalyst may be any hydrogenation catalyst that is effective for the reduction of an aromatic ring. In some embodiments, for example, the aryl hydrogenation catalyst can include a Group VIII metal (Groups 8, 9, and 10 according to IUPAC numbering) supported on a catalyst support material containing carbon, silica, alumina, silica-alumina, zirconium oxide (zirconia), titanium dioxide (titania), chromium oxides, graphite, silicon carbide, or combinations thereof. In some embodiments, the support material in the aryl hydrogenation catalyst is selected from carbon, silicon carbide, graphite and zirconium oxide or combinations thereof. In some embodiments, the support material in the aryl hydrogenation catalyst is selected from carbon, silicon carbide and graphite. In some embodiments, the support material is carbon. Some examples of carbon support materials include activated carbon, carbon nanotubes, carbon powder, carbon rods, carbon black carbon soot and carbon nanofibers. In some embodiments, the carbon support material is selected from carbon nanotubes and activated carbon. In some embodiments, the carbon support material is activated carbon.

In some embodiments, the Group VIII metal in the aryl hydrogenation catalyst is ruthenium. In some embodiments, the Group VIII metal in the aryl hydrogenation catalyst is rhodium. In some embodiments of the present invention the total amount of Group VIII metal present may be about from about 0.1 to about 10 weight percent based on the total weight of the aryl hydrogenation catalyst (i.e. including support). Embodiments exist for a wide variety of such ranges. The lower limit of such ranges may be about 0.1, about 0.2, about 0.3, about 0.4, about 0.5, about 0.6, about 0.7, about 0.8, about 0.9, about 1.0, about 2.0, about 3.0, about 4.0, about 5.0, about 6.0, about 7.0, about 8.0 or about 9.0. The upper limit of such ranges may be about 0.2, about 0.3, about 0.4, about 0.5, about, 0.6, about 0.7, about 0.8, about 0.9, about 1.0, about 2.0, about 3.0, about 4.0, about 5.0, about 6.0, about 7.0, about 8.0, about 9.0 or about 10.0. The range of the weight percent of the Group VIII metal may be any combination of any of the foregoing lower limits with any of the foregoing upper limits. For example, in some embodiments the aryl hydrogenation catalyst can contain from about 2.0 to about 8.0 weight percent rhodium supported on carbon. In some embodiments of the present invention the catalyst can contain from about 0.5 to about 5.0 weight percent ruthenium on carbon wherein the weight percentages are based on the total weight of the aryl hydrogenation catalyst, i.e., the total weight of the support material plus the Group VIII metal.

The aryl hydrogenation catalyst may be in any conventional form such as, for example, in the form of extrudates, granules, and pellets for use in fixed-bed reactor processes and powder for slurry processes. The shape of the supports may be, but are not limit to, cylinders, spheres, stars or any type of multiple-lobe shapes. Depending on the particular support material employed and/or the method used to prepare an aryl hydrogenation catalyst, the Group VIII metal may be deposited primarily on the surface of the support or distributed substantially throughout the support.

The aryl hydrogenation catalyst may be prepared by conventional techniques such as impregnation of one or more Group VIII metals or Group VIII metal compounds on or into the support material. The Group VIII metals may be provided as zero valent metals or as oxidized metals in the form of compounds such as salts of inorganic or organic acids and organometallic complexes. In some embodiments, the Group VIII metal is present as a zero valent metal. In some embodiments, the support materials may be impregnated with one or more Group VIII metals by immersing the support material in a solution of a Group VIII metal compound in a suitable solvent such as water or an organic solvent. The support material then is dried and the metal compound is reduced to a Group VIII metal.

The benzenecarboxylic acid compound, solvent and hydrogen are combined in the presence of the aryl hydrogenation catalyst under conditions effective to cause hydrogenation of the benzene ring. In some embodiments, the pressure in the reactor is from about 80 to about 2,000 pounds per square inch gage (psig) and the temperature in the reactor is from about 20° C. to about 200° C. In some embodiments the temperature is from about 60° C. to about 180° C. In some embodiments in which at least one Group VIII metal used in the aryl hydrogenation catalyst is ruthenium, the temperature is from about 120° C. to about 200° C., and in some such embodiments the temperature is from about 120° C. to about 160° C. In some embodiments in which at least one Group VIII metal used in the aryl hydrogenation catalyst is rhodium, the temperature is from about 80° C. to about 200° C., and in some such embodiments the temperature is from about 80° C. to about 150° C., or from about 90° C. to about 120° C.

In some embodiments the pressure is from about 50 psig to about 3000 psig, in some embodiments the pressure is from about 300 psig to about 2500 psig, in some embodiments the pressure is from about 500 psig to about 3000 psig and in some embodiments from about 500 to about 2000. In some embodiments in which at least one Group VIII metal used in the aryl hydrogenation catalyst is ruthenium, the pressure is from about 1000 psig to about 3000 psig, in some such embodiments the pressure is from about 1200 psig to about 2500 psig, in some such embodiments the pressure is from about 1200 psig to about 2200 psig, in some such embodiments the pressure is from about 1300 psig to about 2100 psig and in some such embodiments the pressure is from about 1300 psig to about 2600 psig. In some embodiments in which at least one Group VIII metal used in the aryl hydrogenation catalyst is rhodium, the pressure is from about 15 psig to about 800 psig, in some such embodiments the pressure is from about 15 to about 600 psig, in some such embodiments the pressure is from about 50 to about 600 psig, in some such embodiments the pressure is from about 50 to about 150 psig, in some such embodiments the pressure is from about 100 to about 250 psig, in some such embodiments the pressure is from about 100 to about 250 psig, in some such embodiments the pressure is from about 80 psig to about 800 psig, in some such embodiments the pressure is from about 80 to about 600 psig, in some such embodiments the pressure is from about 400 to about 600 psig, in some such embodiments the pressure is from about 80 to about 150 psig, in some such embodiments the pressure is from about 150 to about 250 psig and in some such embodiments the pressure is from about 150 to about 250 psig. Any combination of the above temperature and pressure ranges in the previous two paragraphs may be used.

The benzenecarboxylic acid and solvent may be fed to the hydrogenation process by any workable means (i.e. together or separately as workable). In some embodiments, the benzenecarboxylic acid is dissolved or dispersed in the solvent and the two are fed together. Any workable concentration of the benzenecarboxylic acid in solvent may be used. In some embodiments, the mixture contains from about 5 to about 60 wt. % benzenecarboxylic acid. In some embodiments, the amount is from about 5 to about 40 wt. %, from about 10 to about 20 wt. %, from about 10 to about 30 wt. %, from about 20 to about 40 wt. %, from about 10 to about 50 wt. %, from about 30 to about 40 wt. %, from about 10 to about 30 wt. %, from about 20 to about 60 wt. %, from about 20 to about 50 wt. %.

The hydrogenation of benzenecarboxylic acids of the present invention can be carried out in any suitable batch reactor or continuous reactor, such as pressurized fixed bed reactors, multitubular fixed bed reactors, continuous stirred tank reactors, radial flow reactors, plug flow reactors, fluidized bed reactors, jet loop reactors, trickle bed reactors, bubble column reactors. In some embodiments, the duration or contact of the benzenecarboxylic acid with the hydrogen and the aryl hydrogenation catalyst is from about 0.25 to about 10.0 hours, in some embodiments from about 1.0 to about 6.0 hours, in some embodiments from about 2.0 to about 4.0 hours, in some embodiments from about 0.1 hour to about 2.0 hours, in some embodiments from about 0.1 hour to about 1.0 hour and in some embodiments from about 0.2 hour to about 0.8 hour.

The process may be operated at any weight hour space velocity that is useful to the process. Weight hour space velocity is the ratio of mass feed rate for TPA (unit weight per hour) to mass of catalyst (including support). In some embodiments, the weight hour space velocity is from about 0.1 to about 2.0. Embodiments also exist in which the weight hour space velocity is from about 0.1 to about 1.0, or from about 0.1 to about 0.5.

Hydrogenation of the benzenecarboxylic acid produces a cyclohexanecarboxylic acid. As used throughout this application, "cyclohexanecarboxylic acid" means a cyclohexane compound in which at least one of the carbons in the cyclohexane ring has at least one carboxylic acid group bonded thereto. Some examples include compounds that can be produced by hydrogenation of the benzene ring of any of benzenecarboxylic acids discussed above. In some embodiments, cyclohexanecarboxylic acids include the monoacid cyclohexanecarboxylic acid and diacids such as 1,4-cyclohexanedicarboxylic acid and 1,3-cyclohexanedicarboxylic acid or triacids such as 1,3,5-cyclohexanetricarboxylic acid or 1,2,5-cyclohexanetricarboxylic acid. In embodiments in which the "cyclohexanecarboxylic acid" is a diacid, the diacid may be described by its cis/trans ratio, in reference to the relative positions of the two acid groups in relation to the cyclohexane ring. In some embodiments of the invention, the cis/trans ratio of the resulting cyclohexanedicarboxylic acid is from about 3.0 to about 5.2, in some embodiments from 3.0 to 4.5 and in some embodiments from about 4.0 to about 5.0.

Hydrogenation of Cyclohexanecarboxylic Acids

The invention also provides processes that include hydrogenation of at least one carboxylic acid group on at least one cyclohexanecarboxylic acid compound. In such embodiments, the process includes contacting the at least one cyclohexanecarboxylic acid compound with the solvent and hydrogen in the presence of an acid hydrogenation catalyst to form a hydroxymethylcyclohexane compound. The solvent includes tertiary cyclic amide solvent compound and is otherwise as described above. Optionally, a promoter may also be present.

Any cyclohexanecarboxylic acid compound (as described above) may be used in this process. The solvent may be any of the solvents described above, and specifically includes the tertiary cyclic amide solvent compound. The acid hydrogenation catalyst may be any hydrogenation catalyst that is effective for the reduction of a carboxylic acid group to a hydroxymethyl group (i.e. $CH_2OH$). In some embodiments, the acid hydrogenation catalyst is a homogeneous catalyst that is dissolved or dispersed in the solvent. In some embodiments, the catalyst composition includes: (a) a ruthenium, rhodium, iron, osmium or palladium compound; and (b) an organic phosphine. In some embodiments, the catalyst of the present invention is a ruthenium catalyst. The ruthenium compound is not particularly limiting and can be any ruthenium source that is soluble in the solvent of the invention. Some example compounds include ruthenium salts, hydride complexes, carbonyl compounds, halides, oxides, phosphine complexes, and combinations of two or more of the foregoing. Suitable ruthenium salts include ruthenium carboxylates and acetylacetonates. For example, the ruthenium compound can include the acetonylacetonate complex of ruthenium(III). In some embodiments, the ruthenium compounds can be converted to active species under the reaction conditions, such as nitrates, sulfates, carboxylates, beta diketones, and carbonyls. Ruthenium oxide, carbonyl ruthenates and complex compounds of ruthenium, including hydridophosphineruthenium complexes, may also be used. Some examples include ruthenium nitrate, ruthenium dioxide, ruthenium tetroxide, ruthenium dihydroxide, ruthenium acetylacetonate, ruthenium acetate, ruthenium maleate, ruthenium succinate, tris-(acetylacetone)ruthenium, triruthenium dodecacarbonyl, tetrahydrido(decacarbonyl)tetraruthenium, hydrido(undecacarbonyl)triruthenate cyclo-pentadienyl(dicarbonyl)ruthenium dimer, (norbornadiene)bis(methallyl)ruthenium, (cyclooctadiene)bis(methallyl)ruthenium, bis(ethylene)bis(methallyl)ruthenium, ruthenium dioxide, ruthenium tetraoxide, ruthenium dihydroxide and bis(tri-n-butylphosphine)tricarbonylruthenium.

In some embodiments, the ruthenium compound is a tridentate phosphine. Some examples of tridentate phosphine compounds include tris-1,1,1-(diphenylphosphinomethyl)methane, tris-1,1,1-(diphenylphosphinomethyl)ethane, tris-1,1,1-(diphenylphosphinomethyl)propane, tris-1,1,1-(diphenylphosphino-methyl)butane, tris-1,1,1-(diphenylphosphinomethyl)2,2dimethylpropane, tris-1,3,5-(diphenylphosphinomethyl)cyclohexane, tris-1,1,1-(dicyclohexylphosphinomethyl)ethane, tris-1,1,1-(dimethylphosphinomethyl)ethane, tris-1,1,1-diethylphosphinomethyl)ethane, tris-1,1,1-(dimethylphospholylmethyl)ethane, 1,5,9-triethyl-1,5-9-triphosphacyclododecane, 1,5,9-triphenyl-1,5-9-triphosphacyclododecane, tris(2-diphenylphosphinoethyl)amine, and tris(diisopropylphosphinomethyl)amine. In some embodiments, tris-1,1,1-(diphenylphosphinomethyl)-ethane is used. Advantageous results can be achieved with tridentate facially capped phosphines such as tris-1,1,1-(diarylphosphinomethyl)alkane and tris-1,1,1-(dialkylphosphinomethyl)alkane.

In some embodiments, the catalyst composition includes: (a) a ruthenium compound; (b) a tridentate triphosphine compound selected from 1,1,1-tris(diarylphosphinomethyl)alkyl or substituted alkyl; and (c) a promoter selected from Lewis acids, protic acids having an ionization constant ($K_i$) of $5 \times 10^{-3}$ or greater, onium salts, and combinations of two or more of the foregoing; wherein the catalyst components. In some embodiments, (a) and (b) are the same compound.

In some embodiments, the tridentate triphosphine is selected from 1,1,1-tris(diarylphosphinomethyl)alkyl and substituted alkyl. The alkyl substituent can have 1 to 40 carbon atoms. Some examples of alkyl groups include methyl, ethyl, propyl, butyl, pentyl, isobutyl, isopropyl, isopentyl, and the like. The alkyl group can be substituted with any group that does not interfere with the hydrogenation reaction such as, for example, hydroxyl, ether, halogen, sulfonic acid, carboxylic acid, and the like. The aryl group of the tridentate triphosphine compound may have from 6 to 20 carbon atoms. Some examples of the aryl groups include carbocyclic aryl groups such as phenyl, naphthyl, anthracenyl, and substituted derivatives thereof in which one or more substituent groups can replace hydrogen at any carbon position on the aromatic ring(s). Some examples of substituent groups include one or more groups selected from alkyl, alkoxy, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms.

Some representative examples of substituted aryl groups include 2-fluorophenyl, 2,3,4,5,6-pentafluorophenyl, 3,5-bis(trifluoromethyl)phenyl and the like; a mono- or di(hydroxy) aryl radical such as 4-hydroxyphenyl, 3-hydroxyphenyl, 2,4-dihydroxyphenyl, and the like; for example, 4-cyanophenyl; a mono- or di(lower alkyl)aryl radical such as 4-methylphenyl, 2,4-dimethylphenyl, 2-methylnaphthyl, 4-(isopropyl)phenyl, 4-ethylnaphthyl, 3-(n-propyl)phenyl and the like; a mono- or di(alkoxy)aryl radical, for example, 2,6-dimethoxyphenyl, 4-methoxyphenyl, 3-ethoxyindenyl, 4-(isopropoxy)phenyl, 4-(t-butoxy)phenyl, 3-ethoxy-4-methoxyphenyl and the like; 3- or 4-trifluoromethylphenyl, a mono- or dicarboxyaryl radical such as 4-carboxyphenyl, 4-carboxynaphthyl; a mono- or di(hydroxymethyl)aryl radical such as 3,4-di(hydroxymethyl)phenyl, a mono- or di(aminomethyl)aryl radical such as 2-(aminomethyl)phenyl, or a mono- or di(methylsulfonylamino)aryl radical such as 3-(methylsulfonylamino)naphthyl. In some embodiments, for example, tridentate triphosphine compound can be selected from 1,1,1-tris(diphenylphosphinomethyl)alkyl and substituted alkyl. In some embodiments, the ruthenium compound can be selected from ruthenium salts, hydride complexes, carbonyl compounds, halides, oxides, phosphine complexes, and combinations of two or more of the foregoing; and the tridentate triphosphine compound can be selected from 1,1,1-tris(diphenylphosphinomethyl)alkyl and substituted alkyl. In some embodiments, the tridentate triphosphine is 1,1,1-tris(diphenylphosphinomethyl)ethane (also known as TRIPHOS).

Optionally, the rate of reaction can be enhanced by the addition of a promoter selected from Lewis acids, protic acids having an ionization constant ($K_i$) of $5 \times 10^{-3}$ or greater, and onium salts. The term "Lewis Acid", as used herein, refers to the Lewis concept of acid-base equilibria as elaborated in Chemical Reviews, 69, 251 (1969). An example of a Lewis acid promoter includes zinc acetonylacetonate.

Where used, onium salt promoters can include an anionic component that is derived from a strong acid having an ionization constant ($K_i$) of $5 \times 10^{-3}$ or greater such as, for example, phosphoric acid, hexafluorophoshoric acid, hydrobromic acid, tetrafluoroboric acid, trifluoroacetic acid, p-toluenesulfonic acid, triflic acid, sulfuric acid, combinations of two or more of the foregoing, and the like. These anions are neutral to weak bases in comparison to anions such as, for example, hydroxides, carbonates, bicarbonates, and carboxylates without electron-withdrawing substituents. In some embodiments, the onium salt promoters can include a non-coordinating anion. Some examples of onium salt promoters include ammonium hexafluorophosphate, tetrabutylammonium hexafluorophosphate, tetraphenylphosphonium bromide, ammonium tetrafluoroborate, tetramethyl ammonium tetrafluoroborate, combinations of two or more of the foregoing and the like.

Some examples of protic acids having an ionization constant ($K_i$) of $5 \times 10^{-3}$ or greater include toluenesulfonic acid, phosphoric acid, triflic acid, sulfuric acid, methanesulfonic acid, trifluoroacetic acid, dodecylbenzenesulfonic acid, dinonylnaphthalenesulfonic acid, and the like. In some embodiments, the promoter is selected from tetrabutylammonium hexafluorophosphate, triflic acid, toluenesulfonic acid, dodecylbenzenesulfonic acid, dinonylnaphthalenesulfonic acid, and combinations of two or more of the foregoing. Combinations of any one of the above Lewis acids, protic acids, and onium salts also may be used.

The cyclohexanecarboxylic acid compound, solvent and hydrogen are combined in the presence of the acid hydrogenation catalyst (and optional promoter) under conditions effective to cause hydrogenation of the carboxylic acid groups. In some embodiments, the pressure in the reactor is from about 500 to about 5,000 psig and the temperature in the reactor is from about 100° C. to about 250° C. In some embodiments the temperature is from about 150° C. to about 225° C. In some embodiments the temperature is from about 100° C. to about 200° C. In some embodiments the temperature is from about 100° C. to about 150° C. In some embodiments the temperature is from about 160° C. to about 210° C. In some embodiments the pressure is from about 1200 psig to about 3000 psig, in some embodiments the pressure is from about 1000 psig to about 6000 psig, in some embodiments the pressure is from about 500 psig to about 3000 psig, in some embodiments the pressure is from about 1000 psig to about 2500 psig, in some embodiments the pressure is from about 1000 psig to about 2500 psig, in some embodiments the pressure is from about 1500 psig to about 2000 psig, in some embodiments the pressure is from about 1400 psig to about 2000 psig and in some embodiments from about 1400 to about 1600 psig. Combinations of any of the above temperature and pressure ranges are within the scope of the invention.

The hydrogenation of cyclohexanecarboxylic acids of the present invention can be carried out in any suitable batch reactor or continuous reactor, such as pressurized, continuous stirred tank reactors or bubble column reactors. In some embodiments, the duration or contact of the benzenecarboxylic acid with the hydrogen and the aryl hydrogenation catalyst is from about 0.5 to about 20 hours, in some embodiments from about 2 to about 15 hours and in some embodiments from about 4 to about 12 hours. In some embodiments, the weight hour space velocity is from about 0.1 to about 3.0. Embodiments also exist in which the weight hour space velocity is from about 0.5 to about 2.0, or from about 0.75 to about 1.5.

The reaction converts at least some of the at least one cyclohexanecarboxylic acid compound to a hydroxymethylcyclohexane compound. The hydroxymethylcyclohexane product is simply the product formed by replacing one or more carboxylic acid groups with hydroxyl groups. Some examples include cyclohexylmethanol, 1,4-cyclohexanedimethanol, 1,3-cyclohexanedimethanol, 1,2-cyclohexanedimethanol, 1,3,5-cyclohexanetrimethanol and combinations of any two or more of the foregoing. In some embodiments, the at least one hydroxymethylcyclohexane compound is 1,4-cyclohexanedimethanol. In some embodiments, the at least one hydroxymethylcyclohexane compound is 1,3-cyclohexanedimethanol. In some embodiments, the at least one hydroxymethylcyclohexane compound is a combination of 1,3-cyclohexanedimethanol and 1,4 cyclohexanedimethanol.

In embodiments in which the feed cyclohexanecarboxylic acid is a diacid, the resulting hydroxymethylcyclohexane compound may be described by its cis/trans ratio, in reference to the relative positions of the two hydroxymethyl groups in relation to the cyclohexane ring. In some embodiments of the invention, the cis/trans ratio of the resulting hydroxymethylcyclohexane compound is from about 0.20 to about 5.00. Embodiments exist in which the cis/trans ratio is from about 0.60 to about 1.00, from about 0.20 to about 1.00, from about 1.00 to about 1.50, from about 1.00 to about 2.00, from about 2.00 to about 3.00, from about 1.00 to about 3.00, from about 1.50 to about 2.50, from about 2.00 to about 4.00, from about 1.50 to about 3.50, from about 1.50 to about 2.00, from about 2.00 to about 2.50, from about 2.00 to about 3.50, from about 3.00 to about 3.50, from about 3.00 to about 4.50, from about 3.00 to about 5.00, and from about 3.50 to about 5.00.

Additional Process Steps

The process can further involve using separation zones or separation processes to provide a product stream having a desired composition. For example, where a dissolved or other homogeneous catalyst is used, separation techniques may be used to separate the product and solvent from the catalyst. Any useful separation technique can be used. Some examples include vapor stripping, flash distillation, liquid-liquid extraction and membrane separation. For example, DURAMEM 150 membranes available from Evonik Industries have been observed to be effective to separate Ruthenium TRIPHOS catalyst from some hydroxymethylcyclohexane product compositions when used, for example, in stirred cell filters such as those available from Sterlitech Corporation. The catalyst, once separated from the product, can optionally be returned to a reaction zone or process for reuse. Alternatively, the catalyst solution can be diluted with an alcohol solvent such as methanol or ethylene glycol and reused. As another alternative, the reaction mixture can be partitioned between an aqueous phase and an organic phase, which will dissolve the catalyst components. The hydroxymethylcyclohexane compound product can then be recovered from the aqueous phase by simple distillation while the organic phase can be returned to the reactor for reuse. It is understood that the separation process described above can be combined with any of the various embodiments of the inventive process described herein.

The process may also include processes or zones to separate one or more resulting product stream from at least some of the solvent and to further purify the product stream. For example, a separation process can concentrate the product compound (e.g. a cyclohexanecarboxylic acid compound or a hydroxymethyl cyclohexane compound) in a product stream and concentrate solvent into a recovered solvent stream. By "concentrating" a product compound, it is meant that the weight percent of product compound present in product stream is higher than that in the stream fed to the separation process or zone. Similarly, by "concentrating" a solvent compound, it is meant that the weight percent of solvent compound present in a recovered solvent stream is higher than that in the stream fed to the separation process or zone. Any useful separation zone or process can be used. Some examples of separation processes that may be used in some embodiments include distillation, filtration, crystallization and extraction and combinations thereof. Some examples of separation zones that can be used include vessels or equipment that can perform any of the foregoing processes. Recovered solvent may be optionally recycled for reuse in the process. Additional product refining and purification may occur (for example, through another separation process or zone), or separation into more than two streams can be achieved in a single process. In some embodiments of processes involving an aryl hydrogenation step followed by an acid hydrogenation step separation zones or processes may or may not be used between the two hydrogenation steps. In embodiments in which catalyst materials are also separated from one or more streams, the solvent separation can occur before, during or after a catalyst separation process. In some embodiments, catalyst is separated from the product stream in a first separation zone and solvent is separated from the product stream in a second separation zone. In some embodiments, the order is reversed. In some embodiments, catalyst and solvent is separated from the product stream in a single separation zone. In some embodiments, one or more of the foregoing separation zones further serves to separate additional materials.

Product streams may be processed further to obtain desired final compositions. Thus, for example, products may be processed further in one or more additional separation zones of any of the types described above.

Processes Involving Two Hydrogenation Steps

The invention further provides processes that include both of the two types of hydrogenation processes described above. Such processes involve first hydrogenating at least one benzenecarboxylic acid compound to form at least one cyclohexanecarboxylic acid compound, then hydrogenating at least some of the cyclohexanecarboxylic acid compounds to form hydroxymethylcyclohexane compounds. Both steps occur in the presence of a solvent containing at least one tertiary cyclic amide solvent compound. In some embodiments, at least some of the solvent from the first hydrogenation step is reused in the second hydrogenation step without separating it from the cyclohexanecarboxylic acid compounds. In some embodiments, at least about 30% of the solvent from the first hydrogenation step is fed to the second hydrogenation step. In some embodiments, this amount is at least about 50%, at least about 75%, at least about 85%, at least about 90% or at least about 95% of the solvent used in the first hydrogenation step. In some embodiments, the weight percent of total tertiary cyclic amide solvent compounds in the reaction composition of the second step is within about 50 percentage points of the weight percent of total tertiary cyclic amide solvent compounds in the reaction composition first step. In some embodiments, this weight percentage in the second step is within about 40, within about 30, within about 25, within about 20, within about 15 or within about 10 percentage points of the weight percent in the first step. As used throughout this application, weight percentages in a reaction composition refers, in the case of a continuous process, to the weight percentages of materials during steady state operation of the continuous reaction process. In the case of a batch process weight percentages in a reaction composition refers to the total mass of liquid materials fed to the batch process.

One example of such two-step hydrogenation processes is depicted in FIG. 1, in which the first step is the hydrogenation of the aromatic ring of terephthalic acid dissolved in N-methyl-2-pyrrolidone (NMP) to yield 1,4-CHDA and the second step is the hydrogenation of the carboxylic acid groups to hydroxymethyl groups yielding 1,4-CHDM. NMP is then stripped from the product and optionally recycled and the molten product stream is distilled to provide a purified CHDM stream. In this process the feed stream 10 contains TPA (20-30 wt. %) dissolved in NMP (either entirely fresh NMP, stream 135, which also contains low boiling components from stripping column 130, or a combination of the two). The concentration of TPA is 20-30 wt. % in NMP. Feed stream 10 optionally contains a small amount of a secondary alcohol such as isopropanol (5-20 wt. %). Stream 10 is gravity fed to first hydrogenation reactor 20, which is a packed column containing heterogeneous catalyst (or alternately in another configuration allowing intimate mixing of stream 10 with the catalyst under a pressure of hydrogen). Hydrogen 15 is fed to first hydrogenation reactor 20 at a pressure of 1,000 to 1,500 psig. The temperature in first hydrogenation reactor 20 is maintained at 80 to 190° C. The catalyst is a supported zero valent ruthenium metal on a carbon, or other acid-stable, support. The supported catalyst contains 1.0 wt. % ruthenium. The product solution 30 of reactor 20 contains primarily CHDA in NMP. The residence time in 20 is designed to achieve a conversion of greater than 95% to CHDA. Underflow stream 30 is pumped into a second hydrogenation reactor 60. Where desired, a portion of the CHDA produced can be removed with solvent from the process as stream 40 without hydrogenation to CHDM. A feed solution 50 of Ruthenium TRIPHOS (or optionally, a tridentate tridentate compound and a ruthenium compound), optionally accompanied by a promoter, also in the NMP solvent, is pumped into second hydrogenation reactor 60 at a rate and concentration which maintains the concentration of ruthenium in the reactor relatively constant and compensates for the removal of ruthenium from ruthenium-recovery in stream 115. A vapor stream of hydrogen 35 is fed to second hydrogenation reactor 60 at a pressure of 1,500-2,500 psig while temperature is maintained at 160-210° C. The flow of stream 30 into second hydrogenation reactor 60 is designed to maintain a residence time in second hydrogenation reactor 60 adequate to attain a conversion of CHDA to CHDM of greater than 95%. Stream 70 is a liquid overflow removed from second hydrogenation reactor 60 and contains CHDM and Ruthenium TRIPHOS in NMP. This stream is pumped through a membrane filter 80 selected to retain the ruthenium-based hydrogenation catalyst in a retentate solution 100 and permeate a crude product stream 90 containing CHDM and NMP. Optionally, retentate stream 100 is recycled to second hydrogenation reactor 60. Also optionally, a fraction 105 of retentate stream 100 is pumped to a catalyst reactivation reactor 110 and following reactivation treatment a reactivated stream 120 is recombined with stream 100 and pumped into second hydrogenation reactor 60. A slip-stream, 115, is withdrawn from catalyst reactivation reactor 110 to be processed to recover ruthenium for reuse. The rate of removal of ruthenium from the process is governed by the rate of removal of stream 115 from catalyst reactivation reactor 110. Product-containing permeate stream 90 is fed to a solvent stripping distillation column 130, operated at a temperature of 70-100° C. and pressure of 5-20 torr. Solvent stripping distillation column 130 separates a lower-boiling stream 135 containing primarily NMP from a higher boiling product stream 140. The temperature of stripping is selected in order to give appropriate viscosity to crude product stream 140. Lower-boiling stream 135 is optionally recycled to first hydrogenation reactor 20 by combining it with feed 10 (as shown in dotted line) or feeding it separately (not shown). Crude product stream 140 is then processed to recover CHDM in low pressure distillation column 150. A lower-boiling stream containing CHDM product 160 is recovered from the top of low pressure distillation column 150 and a distillation heel, 180, is recycled to solvent stripping distillation column 130 by combining with stream 90 or by feeding directly (not pictured) to column 130. A slip stream 170 is removed from 180 as desired to maintain the fluid properties of stream 180.

In an alternative embodiment, the catalyst in the packed bed in the first hydrogenation reactor 20 is supported zero valent rhodium metal supported on a carbon, or other acid-stable, support. The supported catalyst contains 5 wt. % rhodium. In this embodiment, the pressure in first hydrogenation reactor 20 is 400-600 psig and the temperature is 90-120° C. Optionally, in embodiments in which isopropanol is fed to the first hydrogenation reactor, the pressure is 150-250 psig.

In a different alternate embodiment (not pictured) the NMP is replaced with a solvent that has a higher boiling point than CHDM (for example, 1-(2-hydroxyethyl)-2-pyrrolidone) and the functions of columns 130 and 150 are combined into a single column (not pictured) that is operated at conditions to recover CHDM in an overhead product stream and to recycle the solvent as part of the distillation heel. This embodiment may be practiced with either the ruthenium or the rhodium catalyst embodiments described above.

In another alternative embodiment, functions of columns 130 and 150 are combined into a single column in which NMP is removed as a low boiling fraction (and optionally recycled), higher boiling impurities are removed through an underflow or distillation heel (and optionally recycled) and product is removed as an intermediate stream such as a sidedraw between the two streams.

Resulting Compositions

The invention further provides compositions that contain at least one cyclohexanecarboxylic acid compound of the type described above and at least one cyclic amide solvent compound of the type described above. Any combination of the two described above may be in the composition including all compositions that can result from the processes described herein. Thus, in some embodiments, the composition includes any combination of one or more additional solvent compounds of the type described above. Similarly, the invention further provides compositions that contain at least one hydroxymethylcyclohexane compound of the type described above and at least one cyclic amide solvent compound of the type described above. Again, combination of the two described above may be in the composition including all compositions that can result from the processes described herein and, in some embodiments, the composition includes any combination of one or more additional solvent compounds of the type described above.

The invention has been described in detail with particular reference to embodiments thereof, but it will be understood that variations and modifications can be effected within the spirit and scope of the invention. This invention can be further illustrated by the following examples of embodiments thereof, although it will be understood that these examples are included merely for purposes of illustration and are not intended to limit the scope of the invention unless otherwise specifically indicated. Unless otherwise indicated, all percentages are by weight.

EXAMPLES

Hydrogenation of Benzenecarboxylic Acids to Cyclohexanecarboxylic Acids

Except as otherwise stated in the individual examples, the following procedures were used for hydrogenation of benzenecarboxylic acids to cyclohexanecarboxylic acids. A 100 ml autoclave configured in a high pressure AUTO-MATE System Model 4590 (H.E.L. Inc., Grand Rapids, Mich.) with a drop-in catalyst basket (volume 7 ml) was used. The catalyst was placed in the basket in an amount equal to the lesser of 2.0 grams or the amount that would fit in the basket. The autoclave was then pressurized to 1500 psig with nitrogen. Nitrogen was slowly vented then the feed manifold to the reactor was then purged twice with by passing hydrogen gas through at atmospheric temperature. To activate the catalyst, the reactor was then purged three times by pressurizing with hydrogen to 150 psig, then venting to ambient pressure each time. Agitation at 450 rpm commenced and the reactor was heated to 150° C. Hydrogen was then added to bring the pressure to 1500 psig then held for 2 hours. The reactor was permitted to cool to room temperature, agitation was stopped and pressure was released. The reactor was then placed in a containment box purged with argon to avoid exposing the autoclave to air during loading. TPA (except where indicated otherwise), 3 g, and 50 grams of solvent (except where indicated otherwise) were charged to the autoclave. The agitator was then restarted and held at 450 rpm for 10 minutes. Nitrogen was slowly vented then the feed manifold to the reactor was then purged twice with hydrogen gas at atmospheric pressure. To the reactor was again purged three times by pressurizing with hydrogen to 150 psig, then venting the pressure then venting to ambient pressure each time. The autoclave was then heated to 140° C., the stirrer speed was increased to 800 rpm and the solution was held under these conditions for 40-50 minutes. After this, the catalyst basket was dropped in and hydrogen was then added to bring the pressure to 1500 psig then held for 4 hours. After 4 hours of reaction, hydrogen feed was discontinued and the autoclave was cooled to room temperature. Agitation was then stopped, pressure released, and the contents removed. The contents of the final product solution were filtered using vacuum filtration to remove any granules of the supported catalyst.

All references to NMP in the Examples are references to 99.5% anhydrous N-methyl-2-pyrrolidone (Sigma Aldrich).

Except where indicated otherwise, all references to CHDA and CHDM refer to 1,4-cyclohexanedicarboxylic acid and 1,4-cyclohexanedimethanol.

Hydrogenation of Cyclohexanecarboxylic Acids to Hydroxymethylcyclohexane

For the hydrogenation of cyclohexanecarboxylic acids of cyclohexanecarboxylic acids to hydroxymethylcyclohexanes, the 100 ml autoclave described above for the benzenecarboxylic acid experiments was used again and the conditions were as described below except where indicated. At atmospheric conditions, 0.25 grams of the catalyst Ruthenium 1,1,1-tris(diphenylphosphinomethyl)ethane (Ruthenium TRIPHOS), 2.0 grams reactant cyclohexanecarboxylic acid and 0.02 grams p-toluene sulfonic acid (PTSA) and 30 grams of solvent were added to the autoclave. The reactor was then pressurized to 1500 psig with nitrogen. Nitrogen was slowly vented. The reactor was then purged two more times by pressurizing with nitrogen to 200 psig, then venting the pressure to atmospheric each time. The manifold to the reactor was then purged twice with hydrogen gas (atmospheric pressure). The reactor was then purged three times by pressurizing with hydrogen to approximately 300 psig, then venting the pressure to atmospheric each time. Agitation at 1000 rpm was then commenced, and hydrogen was then added to bring the pressure to 750 psig. The temperature was then increased to 190° C. while allowing pressure to rise. After passing 185° C., hydrogen pressure was increased to 1500 psig. These conditions (190° C. and 1500 psig) were held for 10 hours of reaction. After 10 hours of reaction, the agitation was stopped and the heat turned off to let the autoclave start cooling. After cooling to room temperature, pressure was released and the contents were twice pressurized with nitrogen gas and vented. The solution was finally discharged from the autoclave and analyzed by GC, and, in some cases, by gas chromatography-mass spectrometry (GC-MS).

Analytical Procedures

All GC data in these examples were measured using the following procedures. A liquid sample of 0.03 g was dissolved in pyridine (200 μl), then reacted with N—O-bis(trimethylsilyl)trifluoroacetamide (BSTFA) at 80° C. for 30 minutes to ensure quantitative derivatization into corresponding trimethylsilyl derivatives. Separation and quantification was done with a GC column and a flame ionization detector (FID). The GC method used a DB-5 capillary column or equivalent (30 meters×0.32 mm ID×0.25 um film thickness), a split injector (at 330° C.), a flame ionization detector (at 300° C.), helium carrier gas at a constant linear velocity of 20.4 cm/sec (a Shimadzu GC 2010 or equivalent) or at an initial column head pressure of 5.7 psig, an oven temperature program of 40° C. initial temperature for 6 min, and 15° C./min temperature ramp to 300° C. for 6.66 min final hold time. A 1-ul sample of this solution was injected with a split ratio of 40:1. The method provided quantification range of 0.01-100 wt. % for each analyte within its separation capability.

Conversion percentages for the benzenecarboxylic acid represent (moles of benzenecarboxylic acids converted divided by initial moles of benzenecarboxylic acids) multiplied by 100. Moles converted are determined by measuring the difference between the number of starting moles and the number of moles at completion. Selectivity percentages for the product cyclohexanecarboxylic acids represent (the final moles of cyclohexanecarboxylic acid divided by the total number of moles of benzenecarboxylic acid converted) multiplied by 100.

CHDA conversion percentages represent (moles of CHDA converted divided by initial moles of CHDA) multiplied by 100. Moles converted are determined by measuring the difference between the number of starting moles and the number of moles at completion. CHDM selectivity percentages represent (the final moles of CHDM divided by the total number of moles of CHDA converted) multiplied by 100.

Mass balances in each example is (the final weight of the solution divided by the initial weight of the solution) multiplied by 100.

Examples 1 and 2

TPA Hydrogenation to CHDA in NMP/Water as a Solvent

The catalyst used was 1% Ru loaded on ¼" carbon granules (1% Ru/C, Lot # SE09051, BASF Corporation, Iselin, N.J.). The solvent in Example 1 was a mixture of 50 parts NMP and 16 parts deionized water. The solvent in Example 2 was NMP. The filtered resultant solution was analyzed by the GC method described above to quantify TPA, CHDA and other byproducts. Results are presented in Table 1 below.

TABLE 1

TPA hydrogenation to CHDA in the presence of NMP as a solvent.

| Example | TPA Conversion % | CHDA Selectivity % | Mass Balance % |
|---|---|---|---|
| 1 | 86 | 71 | 86 |
| 2 | 45 | 96.5 | 93 |

The results shown in Table 1 suggest that NMP is a suitable solvent for highly selective production of CHDA from TPA. In the presence of water, although the conversion increases, the selectivity drops from 96% to 71%, the conversion increases from 45% to 86%. GC-MS was conducted for Example 2. The GC wt. % accountability for Example 2 was 101.4% and the cis/trans ratio of product CHDA was 4.4.

Comparative Examples 1-8

The effect of using other solvents on TPA hydrogenation to CHDA were considered. The procedures of Example 2 were repeated using other liquids with published TPA solubilities greater or less than that of NMP. Results (along with published solubility data, presented in grams of TPA per grams of solvent at 25° C.) are provided in Table 2, along with the results from Examples 1 and 2.

TABLE 2

TPA hydrogenation to CHDA in the presence of other solvents.

| Example | Solvent | Published TPA Solubility In Solvent g/100 g at 25° C. | TPA Conversion % | CHDA Selectivity % | Mass Balance % |
|---|---|---|---|---|---|
| 1 | 50 parts NMP and 16 parts deionized water | | 86 | 71 | 86 |
| 2 | NMP | 5.5$^a$ ~5$^b$ | 45 | 96.5 | 93 |
| Comp 1 | Dimethyl sulfoxide (DMSO) | 20$^c$ | 7 | 5 | 96 |
| Comp 2 | Methanol** | 0.1$^c$ | 60* | 17* | 63 |
| Comp 3 | 1,3-Dimethyl-2-imidazolidinone | | 69 | 16 | 94 |
| Comp 4 | 1,3-Dimethyl-3,4,5,6-tetrahydro 2(1H)-pyrimidinone | | 4 | 7 | 94 |
| Comp 5 | 5-Ethyl-2-methylpyridine | | 15 | 0 | 94 |
| Comp 6 | Dimethylformamide (DMF) | 6.7$^c$ 7.4$^d$ | 95 | 4 | 100 |
| Comp 7 | N,N-Dimethylacetamide (DMAC) | ~3$^b$ | 67 | 45 | 92 |
| Comp 8 | Water** | 0.0019$^c$ | 16 | 20 | 88 |

*GC-MS results indicate that the other species accounting for the conversion of TPA are the mono-methylester and di-methylester of TPA.
**Due to the formation of bi-phasic products, the conversions are based also on the weight of the solid TPA obtained.
$^a$Li, D. Q., et al., "Solubilities of Terephthalaldehydic, p-Toluic, Benzoic, Terephthalic, and Isophthalic Acids in N-Methyl-2-pyrrolidone from 295.65 K to 371.35 K". Chem Eng. Data 46, 172. (2001).
$^b$U.S. Pat. No. 6,113,866
$^c$Published data contained in catalog of design theses at http://www.sbioinformatics.com/design_thesis/Terephthalic_acid/Terephthalic-2520acid_Properties&uses.pdf
$^d$Harper, J. J. and Janik, P., "Terephthalic Acid Solubility" J. Chem Eng. Data 15, 439. (1970).

These data demonstrate that use of even some solvents having higher published solubility than that of NMP resulted in lower yields of CHDA and in some cases, no evidence of catalytic hydrogenation activity was observed.

Example 3

TPA Hydrogenation to CHDA in NEP as a Solvent

Example 2 was repeated but instead of N-methyl 2-pyrrolidone (NMP) as a solvent, N-ethyl 2-pyrrolidone (NEP) was used as a solvent. The GC wt. % accountability for Example 4 was 91.3% and the cis/trans ratio of product CHDA was 4.6.

TABLE 3

TPA hydrogenation to CHDA in the presence of NEP as a solvent.

| Example | Solvent | TPA Conversion % | CHDA Selectivity % | Mass Balance % |
|---|---|---|---|---|
| 3 | NEP | 71.6 | 82.3 | 95 |

As can be seen from the result in Table 3, NEP is a suitable solvent for TPA hydrogenation to CHDA much like NMP.

Examples 4 and 5

Higher Volume Experiments

The experiments were conducted using the Ruthenium on carbon catalyst in a 1000 ml autoclave. A 300 ml autoclave configured in a high pressure AUTO-MATE System Model 4560 (H.E.L. Inc., Grand Rapids, Mich.). These reactions used nine grams of terephthalic acid and 200 grams of a 3:1 mixture of NMP and water. The amount of ruthenium on carbon catalyst was 20 grams in Example 4 and ten grams in Example 5. Procedures were otherwise consistent with Example 2. TPA conversion and CHDA selectivity data are presented in Table 4.

TABLE 4

TPA hydrogenation to CHDA in the presence of NMP as a solvent.

| Example | TPA Conversion % | CHDA Selectivity % |
|---|---|---|
| 4 | 100 | 81 |
| 5 | 100 | 90 |

As seen in Table 4, the catalyst activity is appreciable with 100% conversion of TPA and 90% selectivity to CHDA giving a total yield of 90%.

Comparative Examples 9-10

The procedures of Example 2 were repeated with the following exceptions. Comparative Example 9 was conducted in the absence of hydrogen. The autoclave was pressurized instead with 1500 psig nitrogen instead. Comparative Example 10 was conducted in the absence of the Ru/C catalyst but in the presence of 1500 psig hydrogen. The resulting product solutions were analyzed by GC-MS. In both these experiments, no CHDA was obtained from TPA.

Example 6

IPA Hydrogenation to 1,3-CHDA in NMP

The procedures of Example 2 were repeated except that terephthalic acid was replaced with isophthalic acid (IPA) and the resulting CHDA was 1,3 cyclohexanedicarboxylic acid. Results are presented in Table 5. Attractive conversion and selectivity were achieved.

TABLE 5

IPA hydrogenation to CHDA in the presence of NMP as a solvent.

| Example | IPA Conversion % | CHDA Selectivity % |
|---|---|---|
| 6 | 66 | 93 |

Examples 7-11

TPA Hydrogenation to CHDA in NMP as a Solvent with Other Noble Metals as Catalysts The procedures of Example 2 were repeated replacing the ruthenium on carbon with other supported noble metal catalysts. The reaction parameters are detailed below in Table 6.

For the Rhodium catalyst in Examples 10 and 11, a lower temperature and pressure were used. Use of the Rh/C catalyst with NMP as a solvent resulted in 88% conversion of TPA and 97% selectivity to CHDA at only 500 psig $H_2$ pressure and 100° C. temperature. GC-MS for Example 10 was conducted. The GC wt. % accountability or Example 10 was 100.6% and the cis/trans ratio of product CHDA was 4.7. The GC wt. % accountability for Example 11 was 100% and the cis/trans ratio of product CHDA was 4.0.

TABLE 6

TPA hydrogenation to CHDA in the presence of NMP as a solvent with different catalysts.

| Example | Catalyst | Pressure psig | Temperature ° C. | TPA Conversion % | CHDA Selectivity % | Mass Balance % |
|---|---|---|---|---|---|---|
| 7 | Pd/C* | 1500 | 140 | 7.2 | 5.5 | 92 |
| 8 | Pt/C** | 1500 | 140 | 15.2 | 19.3 | 95 |
| 9 | Ir/C*** | 1500 | 140 | 16.3 | 0 | 96 |
| 10 | Rh/C**** | 500 | 100 | 88.5 | 97 | 94 |
| 11 | Rh/C**** | 1000 | 100 | 47.3 | 97.2 | 96 |

*0.5% Pd/C, CBA300, Lot # SE09101, BASF Corporation, Iselin, NJ, 08830
**5% Pt/C, Sample Code 43220, Lot # 08860, BASF Italia, Rome Italy.
***1% Ir/C, 38330, Lot # E22Y009, Alfa Aesar - A Johnson Matthey Company, Ward Hill, MA,
****5% Rh/C, SO 20337, Lot # 31005, BASF Corporation, Iselin, NJ, 08830

The use of Rh/C catalysts in the presence of NMP as a solvent affords the possibility of running the hydrogenation at lower temperatures and pressures.

Example 12

Increased Concentration TPA Hydrogenation to CHDA in the Presence of NMP as a Solvent Experimental conditions from Example 10 were followed except that instead of only 3 g TPA in 50 g NMP, 6 g TPA was charged to the reactor. Even at this increased concentration of TPA, the final product was a single solution of TPA, CHDA in NMP with no formation of solids. Results are presented in Table 7. GC-MS was conducted. The GC wt. % accountability was 101.2% and the cis/trans ratio of product CHDA was 4.5. The high solubility of TPA in NMP affords the possibility of higher production rates by increasing the concentration of TPA.

TABLE 7

Increased concentration TPA hydrogenation to CHDA in the presence of NMP as a solvent.

| Example | Solvent | TPA Conversion % | CHDA Selectivity % | Mass Balance % |
|---|---|---|---|---|
| 12 | NMP | 77.9 | 95 | 93 |

Examples 13-14

Enhanced TPA Hydrogenation to CHDA in NMP and Isopropanol as a Solvent

The procedures of Example 10 were repeated but the amount of TPA charged to the reactor was 2.75 grams the hydrogen pressure was 200 psig and the reaction was discontinued after 2 hours at 200 psig hydrogen pressure. The solvent in Example 13 was NMP and the solvent in Example 14 was a 9:1 mixture of NMP with isopropanol (anhydrous 99.5% Sigma Aldrich). Results are presented in Table 8 below. As can be seen, although the reaction conditions in Example 13 reduced the TPA conversion, the addition of isopropanol in Example 14 doubled the conversion of TPA with no change in the selectivity to CHDA. The GC wt. % accountability for Examples 13 and 14 were 98.4% and 96.9%, respectively, whereas the cis/trans ratios of product CHDA were 4.8 and 5.4, respectively.

TABLE 8

TPA hydrogenation to CHDA in the presence of NMP/isopropanol as a solvent with Rh/C.

| Example | Solvent | TPA Conversion % | CHDA Selectivity % | Mass Balance % |
|---|---|---|---|---|
| 13 | NMP | 40.8 | 92.8 | 93 |
| 14 | 90% NMP + 10% Isopropanol | 88.5 | 93.1 | 93 |

Example 15

Low Pressure TPA Hydrogenation to CHDA with Ru/C Catalyst

The procedures of Example 13 were repeated, but instead of a Rh/C catalyst the Ru/C catalyst of Example 2 was used. Results are presented in Table 9, rhodium catalyst achieves higher CHDA selectivity and TPA conversion rates under these conditions than the ruthenium.

TABLE 9

TPA hydrogenation to CHDA in the presence of NMP as a solvent with Ru/C.

| Example | Solvent | TPA Conversion % | CHDA Selectivity % | Mass Balance % |
|---|---|---|---|---|
| 15 | NMP | 11.5 | 14.8 | 93 |

Comparative Examples 11-12

Attempted TPA Hydrogenation to CHDA with Other Solvents on a Rh/C Catalyst

These examples illustrate that the different influence of NMP and DMSO as solvents on the activity of ruthenium catalysts is also observed for rhodium catalysts. The procedures of Example 13 were repeated using either DMSO (Comparative Example 11) or DMAC (Comparative Example 12) instead of NMP. No formation of CHDA was observed in Comparative Example 11. With the use of DMAC as a solvent in Comparative Example 12, only 4.8% CHDA was observed.

Example 16-17

Low Pressure Benzoic Acid Hydrogenation in NMP as a Solvent with Rh/C Catalyst

To demonstrate the applicability of the invention to other benzenecarboxylic acid, experiments were conducted involving the selective ring hydrogenation of benzoic acid (BA) to cyclohexanecarboxylic acid (CHCA). The procedures of Example 2 were repeated, but modified as shown in Table 10 below, and with the same amount of benzoic acid in the place of TPA. Results are also presented in Table 10. The GC wt. % accountability for Examples 16 and 17 were 97% and 94%, respectively.

TABLE 10

Benzoic acid hydrogenation in the presence of NMP as a solvent with a Rh/C catalyst.

| Example | Pressure Psig | Temperature °C. | BA Conversion % | CHCA Selectivity % | Mass Balance % |
|---|---|---|---|---|---|
| 16 | 100 | 100 | 99.6 | 93 | 94 |
| 17 | 500 | 100 | 99.6 | 90 | 94 |

Examples 18-20

Resistance of CHDA to Hydrogenation in Catalyst Systems

These following examples were completed to illustrate the stability of CHDA formed in the processes of the present invention. For Examples 18 and 19, the procedures of Example 2 and Comparative Example 1, respectively, were repeated except that CHDA rather than TPA was fed to the reactors. For Example 20, the procedures of Example 13 were repeated except that CHDA rather than TPA was fed to the reactor, the reaction pressure was 200 psig and the reaction time was two hours. The results, presented in Table 11, indicate low levels of CHDA conversion and no detectable formation of CHDM. The cis/trans ratio of CHDA in all three examples were measured at 3.5 both before and after the reaction, indicating no hydrogenation or isomerization of CHDA occurred.

TABLE 11

Attempted CHDA hydrogenation to CHDM in NMP as a solvent with 1 wt. % Ru/C catalyst (Examples 18 and 19) and with a Rh/C catalyst (Example 20).

| Example | Solvent | CHDA Conversion % | CHDM Formed |
|---|---|---|---|
| 18 | NMP | 5.7 | No |
| 19 | DMSO | 7.2 | No |
| 20 | NMP | 2.9 | No |

Examples 21-22

CHDA Hydrogenation to CHDM in NMP and NMP Blend

The above procedures for hydrogenation of cyclohexanecarboxylic acids to hydroxymethylcyclohexanes were followed. The catalyst used was Ruthenium TRIPHOS and the reactant was CHDA. Results are presented in Table 12 below.

TABLE 12

CHDA hydrogenation to CHDM in the presence of NMP as a solvent.

| Example | Reactant | Solvent | Conversion % | CHDM Selectivity % | Cis/Trans Ratio |
|---|---|---|---|---|---|
| 21 | CHDA | NMP - 30 g | 95.6 | 59.7 | 0.99 |
| 22 | CHDA | NMP - 30 g Water - 3 g | 86.6 | 43.2 | 0.7 |

Lower selectivity was observed in Example 22. To understand if the Ruthenium TRIPHOS catalyst was capable of generating products from hydrogenolysis, a GC-MS scan was taken of the product solution. GC-MS results indicated that the catalyst did not convert CHDM to alkanes. The only other byproduct observed in the GC-MS scan was the partially hydrogenated product 4-(hydroxymethyl)cyclohexanecarboxylic acid.

Example 23

CHDA Hydrogenation to CHDM in Ethanol as a Solvent

Example 23 repeated the procedures of Example 21 except that the solvent was ethanol. Results are presented in Table 13 below. The conversions are based on moles of the reactant cyclohexanediacid converted to initial moles of the reactant. The selectivities are based on the final moles of CHDM relative to the reacted moles of the reactant. GC-MS indicated that the other major product is 4-(hydroxymethyl)cyclohexanecarboxylic acid. Decarbonylated products were not observed.

TABLE 13

CHDA hydrogenation to CHDM in the presence of ethanol as a solvent.

| Example | Reactant | Conversion % | CHDM Selectivity % | Cis/Trans Ratio |
|---|---|---|---|---|
| 23 | CHDA | 99.2 | 97.4 | 1.21 |

What is claimed is:

1. A process for making at least one cyclohexanecarboxylic acid compound comprising combining at least one benzenecarboxylic acid compound, at least one solvent and hydrogen in the presence of at least one aryl hydrogenation catalyst under conditions effective to hydrogenate the benzene ring on at least some of the at least one benzenecarboxylic acid compound, wherein the at least one aryl hydrogenation catalyst comprises at least one rhodium or ruthenium compound on a solid support and the at least one solvent comprises at least one tertiary cyclic amide solvent compound.

2. The process of claim 1, wherein the at least one tertiary cyclic amide solvent compound has the structure depicted in formula I or II:

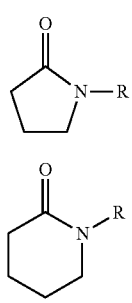

wherein R is selected from alkyl, cycloalkyl, aryl, aryl-substituted alkyl, cycloalkyl-substituted alkyl, alkyl-substituted aryl, and alkyl-substituted cycloalkyl, and wherein R has from 1 to 10 carbon atoms and optionally possesses one hydroxyl group.

3. The process of claim 2, wherein R has one or two carbon atoms.

4. The process of claim 2, wherein R is an unsubstituted alkyl group.

5. The process of claim 4, wherein R is methyl or ethyl.

6. The process of claim 2, wherein R is 2-hydroxyethyl.

7. The process of claim 2, wherein the at least one tertiary amide solvent compound has the structure depicted in formula I.

8. The process of claim 7, wherein R has one or two carbon atoms.

9. The process of claim 7, wherein R is an unsubstituted alkyl group selected from methyl and ethyl.

10. The process of claim 7, wherein R is 2-hydroxyethyl.

11. The process of claim 1, wherein at least about 50% by weight of the solvent is at least one tertiary cyclic amide solvent compound.

12. The process of claim 1, wherein at least about 80% by weight of the solvent is at least one tertiary cyclic amide solvent compound.

13. The process of claim 1, wherein the solvent further comprises isopropyl alcohol.

14. The process of claim 11, wherein the solvent further comprises isopropyl alcohol.

15. The process of claim 1, wherein the at least one benzenecarboxylic acid compound comprises at least one monoacid.

16. The process of claim 1, wherein the at least one benzenecarboxylic acid compound comprises at least one diacid.

17. The process of claim 16, wherein the at least one diacid is selected from terephthalic acid, isophthalic acid, or combinations thereof.

18. The process of claim 16, wherein the at least one diacid is isophthalic acid.

19. The process of claim 16, wherein the at least one diacid is terephthalic acid.

20. The process of claim 3, wherein the at least one benzenecarboxylic acid compound is selected from terephthalic acid, isophthalic acid, or combinations thereof.

21. The process of claim 8, wherein the at least one benzenecarboxylic acid compound is terephthalic acid.

22. The process of claim 8, wherein the at least one benzenecarboxylic acid compound is selected from terephthalic acid, isophthalic acid, or combinations thereof.

23. The process of claim 8, wherein the at least one benzenecarboxylic acid compound is terephthalic acid.

24. The process of claim 1, wherein the at least one cyclohexanecarboxylic acid compound comprises 1,4 cyclohexanedicarboxylic acid.

25. The process of claim 1, wherein the at least one cyclohexanecarboxylic acid compound comprises 1,3 cyclohexanedicarboxylic acid.

26. The process of claim 1, wherein the at least one cyclohexanecarboxylic acid compound comprises 1,3 cyclohexanedicarboxylic acid and 1,4 cyclohexanedicarboxylic acid.

27. The process of claim 1, wherein the at least one aryl hydrogenation catalyst comprises at least one ruthenium compound on a solid support.

28. The process of claim 27, wherein the solid support is carbon.

29. The process of claim 27, wherein conditions effective to hydrogenate the benzene ring on at least some of the at least one benzenecarboxylic acid compound comprise pressure of from about 1,000 to about 1,500 psig and temperature of from about 80 to about 190° C.

30. The process of claim 1, wherein the at least one aryl hydrogenation catalyst comprises at least one rhodium compound on a solid support.

31. The process of claim 30, wherein the solid support is carbon.

32. The process of claim 30, wherein conditions effective to hydrogenate the benzene ring on at least some of the at least one benzenecarboxylic acid compound comprise pressure of from about 400 to about 600 psig and temperature of from about 80 to about 120° C.

33. The process of claim 30, wherein the solvent further comprises isopropyl alcohol and conditions effective to hydrogenate the benzene ring on at least some of the at least one benzenecarboxylic acid compound comprise pressure of from about 150 to about 400 psig and temperature of from about 80 to about 120° C.

* * * * *